United States Patent

Goddard

[11] 4,123,252
[45] Oct. 31, 1978

[54] METHOXY SUBSTITUTED CYCLOALKANAPYRAZOLE HERBICIDES

[75] Inventor: Steven J. Goddard, West Grove, Pa.

[73] Assignee: E. I. Du Pont de Nemours and Company, Wilmington, Del.

[21] Appl. No.: 726,295

[22] Filed: Sep. 24, 1976

Related U.S. Application Data

[63] Continuation-in-part of Ser. No. 649,901, Jan. 16, 1976, abandoned.

[51] Int. Cl.² .............. A01N 9/22; C07D 231/54; C07D 231/56
[52] U.S. Cl. .............. 71/92; 584/359; 548/369; 544/172; 560/126
[58] Field of Search .............. 260/310 R; 71/92

[56] References Cited

U.S. PATENT DOCUMENTS 3,364,227  1/1968  Robinson .............. 71/92
4,008,249  2/1977  Fischer et al. .............. 260/310 R

OTHER PUBLICATIONS

Jacquier et al. Chem. Abst. Vol. 67 1967, 43768g.
Bayer, Chem. Abst. Vol. 60, 6957.
Nunn et al. Chem. Abst. 84 90084S, 1976.

Primary Examiner—Natalie Troujof
Assistant Examiner—Jane T. Fan

[57] ABSTRACT

Herbicidal cyanoalkanapyrazoles of the formula:

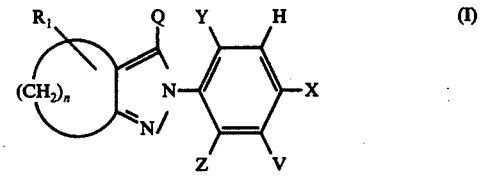

where
  $n$ is 3, 4, or 5;
  Q is —O—CH$_3$ or —S(O)$_m$—CH$_3$;
  where $m$ is 0, 1 or 2; and
  R$_1$ is hydrogen or methyl;
  V is hydrogen, fluorine or chlorine;
  X is fluorine, chlorine, bromine, iodine, cyano or methoxy;
  Y is hydrogen, fluorine, or chlorine; and
  Z is hydrogen or fluorine;
provided that:
  (a) when $n$ is 3, R$_1$ is hydrogen;
  (b) when $n$ is 5, R$_1$ is hydrogen, Y is hydrogen or fluorine, Z and V are hydrogen and X is fluorine, chlorine or bromine and m is 0;
  (c) when V is fluorine or chlorine, X is fluorine, chlorine or bromine and Z is hydrogen;
  (d) when $m$ is 1 or 2, Y is fluorine and V and Z are hydrogen.

53 Claims, No Drawings

METHOXY SUBSTITUTED CYCLOALKANAPYRAZOLE HERBICIDES

RELATED APPLICATION

This application is a continuation-in-part of my co-pending application Ser. No. 649,901, filed Jan. 16, 1976, now abandoned.

BACKGROUND OF THE INVENTION

Recently, in German Offenlegungsschrift 2,165,651 a group of isoindole-1,3-diones which are useful as herbicides was disclosed. The general formula for the isoindole-1,3-diones disclosed in the Offenlegungsschrift is as follows:

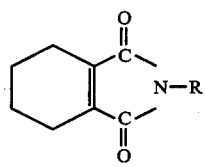

wherein R may be an aryl, aralkyl or benzyl substituent optionally substituted with 1 to 5 halogen atoms or a hydroxy, nitro, cyano, thiocyanato, carboxy, alkyl or halogenated alkyl, alkoxy, lower alkylthio or phenyl group. R may also be optionally substituted with a group having the configuration —O—CH$_2$A where A is a phenyl or a naphthyl group. The phenyl group may be substituted with one or more halogen atoms, nitro groups, lower alkyl groups or lower alkoxy groups.

Typical of the compounds disclosed in the Offenlegungsschrift is the compound of Structure 1.

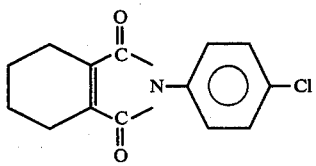

Although the compounds disclosed within the Offenlegungsschrift are active herbicides, the need still exists for even better herbicides. Weeds are very damaging to important crops, such as rice and wheat, and they decrease crop yield. In the current world situation, wherein food shortages are acute, it is important to harvest the maximum possible yields of crops such as rice or wheat. Thus, a need exists for a particularly effective herbicide which will destroy as many weeds as possible without causing significant damge to the desired crops, e.g., rice.

According to the instant invention, compounds have been discovered which are highly active herbicides and yet cause minimal damage to certain desired crops, e.g., rice and wheat, and especially the major world food crop, rice.

The preparation and fungicidal utility of 2-(4-chlorophenyl)-1,2,4,5,6,7-hexahydroindazol-3(3H)-one is disclosed in Takeda Chem. Ind. Paper, Chem. Abs., 67, 11542h (1967).

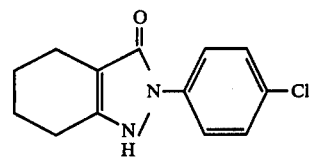

2-Aryl-4,5,6,7-tetrahydro-1-alkyl-1H-indazol-3(2H)-ones are claimed as antipyretics in Ger. 668.628 [assigned to P. Beierdorf & Co. AG, Chem. Abs., 33, 5131$^2$(1939)] and U.S. Pat. No. 2,104,348 [assigned to E. R. Squibb Co., Chem. Abs., 32, 1869$^1$ (1938)].

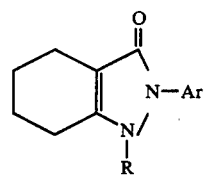

1-Phenyl-3,4-trimethylenepyrazolone is disclosed in U.S. Pat. No. 1,685,407 (1928) with utility as an intermediate for making dyes and medicinal compounds. C. Mannich in Arch. Pharm. 267, 699–702 (1929) and in Brit. 260,577 describes the preparation of 1-phenyl-3,4-trimethylenepyrazolones.

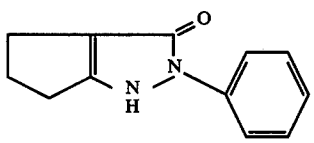

R. P. Williams et al. in J. Med. Chem. 13, 773 (1970) reports the preparation and evaluation as antiinflammatory agents compounds of the following type:

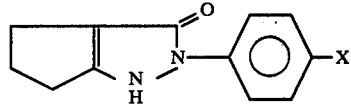

X = H, Br, F.

DESCRIPTION OF THE INVENTION

This invention relates to the novel compounds of Formula I and to agricultural compositions containing them, and to the method of use of these compounds as selective, as well as general, herbicides having both pre- and post-emergence activity.

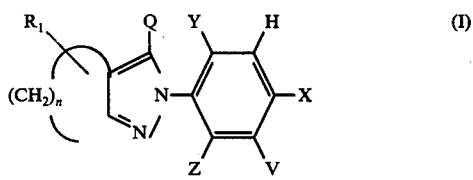

where
n is 3, 4, or 5;
Q is —O—CH$_3$ or —S(O)$_m$—CH$_3$;
where m is 0, 1, or 2; and
R$_1$ is hydrogen or methyl;
V is hydrogen, fluorine or chlorine;

X is fluorine, chlorine, bromine, iodine, cyano or methoxy;

Y is hydrogen, fluorine, or chlorine; and

Z is hydrogen or fluorine;

provided that:

(a) when $n$ is 3, $R_1$ is hydrogen;

(b) when $n$ is 5, $R_1$ is hydrogen, Y is hydrogen or fluorine, Z and V are hydrogen, X is fluorine, chlorine or bromine and $m$ must be 0;

(c) when V is fluorine or chlorine, X is fluorine, chlorine or bromine and Z is hydrogen; and (d) when $m$ is 1 or 2, Y is fluorine and V and Z are hydrogen.

Preferred for their higher herbicidal activity or favorable cost or both are those compounds of Formula I where, independently, (1) $n$ is 3 or 4; or (2) Q is methoxy or methylthio; or (3) Y is hydrogen or fluorine, V is hydrogen and Z is hydrogen; or (4) $R_1$ is hydrogen.

More preferred for their higher herbicidal activity or more favorable cost or both are those compounds of Formula I where $n$ is 3 or 4, Q is methoxy or methylthio and $R_1$ is hydrogen.

Most preferred for their superior activity or highly favorable cost or both are those compounds of Formula I where $n$ is 4, Q is methoxy or methylthio, V is hydrogen, X is fluorine, chlorine or bromine, Y is hydrogen or fluorine, Z is hydrogen and $R_1$ is hydrogen.

Specifically preferred for their outstanding herbicidal activity, highly favorable cost or both are:

(1) 2-(4-chloro-2-fluorophenyl)-4,5,6,7-tetrahydro-3-methoxy-2H-indazole, m.p. 100°–102° C.

(2) 2-(4-chlorophenyl)-4,5,6,7-tetrahydro-3-methoxy-2H-indazole, m.p. 60°–62° C.

(3) 2-(4-chloro-2-fluorophenyl)-4,5,6,7-tetrahydro-3-methylthio-2H-indazole, m.p. 66°–67° C.

SYNTHESIS OF THE COMPOUNDS

The novel cycloalkanapyrazoles of Formula I, where Q is methoxy, are prepared in two steps as shown by Equations A and B:

A.

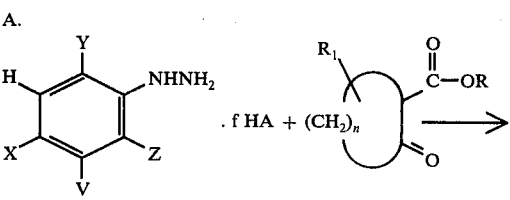

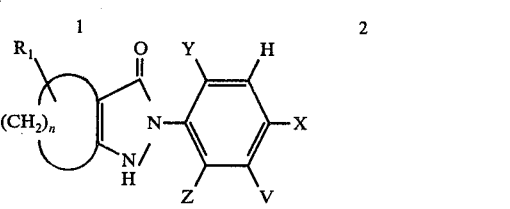

B.

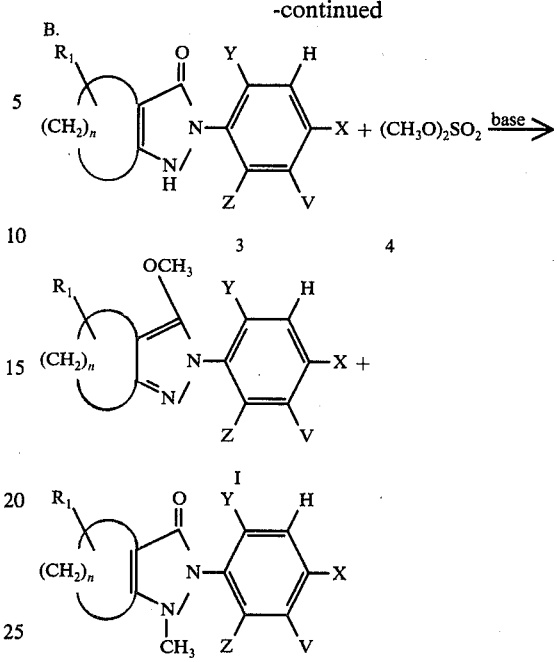

where $n$, $R_1$, V, X, Y and Z are as defined above;

R is alkyl of 1 to 3 carbon atoms;

$f$ is 0 or 1; and

A is an anion of the corresponding acid HA having an ionization constant of at least $1 \times 10^{-7}$, e.g., $H_2SO_4$ or HCl.

The preparation of the annelated pyrazolones 3 is known in the literature; for example, the preparation of 2-aryl-1,2,4,5,6,7-hexahydroindazol-3(3H)-ones (3, $n = 4$) is described in W. Dieckmann, Ann., 317, 102 (1901). The β-keto ester 2 is combined with the appropriate aryl hydrazine acid salt 1 in an appropriate solvent, such as a lower alcohol or aromatic hydrocarbon, and, optionally, in the presence of an acid acceptor, such as a tertiary organic amine or alkali metal hydroxide or alkoxide and the reaction mixture is heated at reflux for 0.5–24 hours. The pyrazolone 3 is isolated by conventional techniques such as by pouring the reaction mass into water and filtering the product. The crude product is usually of sufficient purity to be used directly in the next step. If necessary, further purification can be accomplished by recrystallization, sublimation, or other conventional techniques known to those skilled in the art. This same procedure can be used to prepare those compounds of formula 3 in which $n = 5$.

The pyrazolones 3 where $n$ is 3 are prepared by combining the appropriate aryl hydrazine with the appropriate alkyl 2-oxocyclopentanecarboxylate in a suitable solvent such as toluene or chlorobenzene. The reaction is heated at reflux and water is simultaneously removed to yield a hydrazone. Cyclization to the pyrazolones 3 when $n$ is 3 is then effected by adding 1–3 equivalents of an alkali metal alkoxide such as sodium methoxide to the hydrazone solution and heating for 1–5 hours at 80°–130° C.

Methods taught in Arch. Pharm., 267, 699–702 (1929) and in J. Med. Chem., 13, 773 (1970) are also useful in preparing pyrazolones of formula 3 in which $n = 3$.

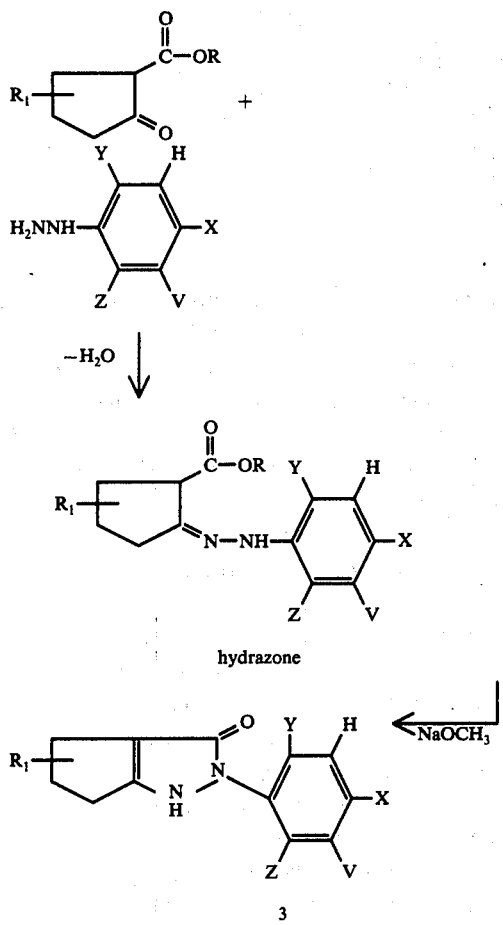

hydrazone

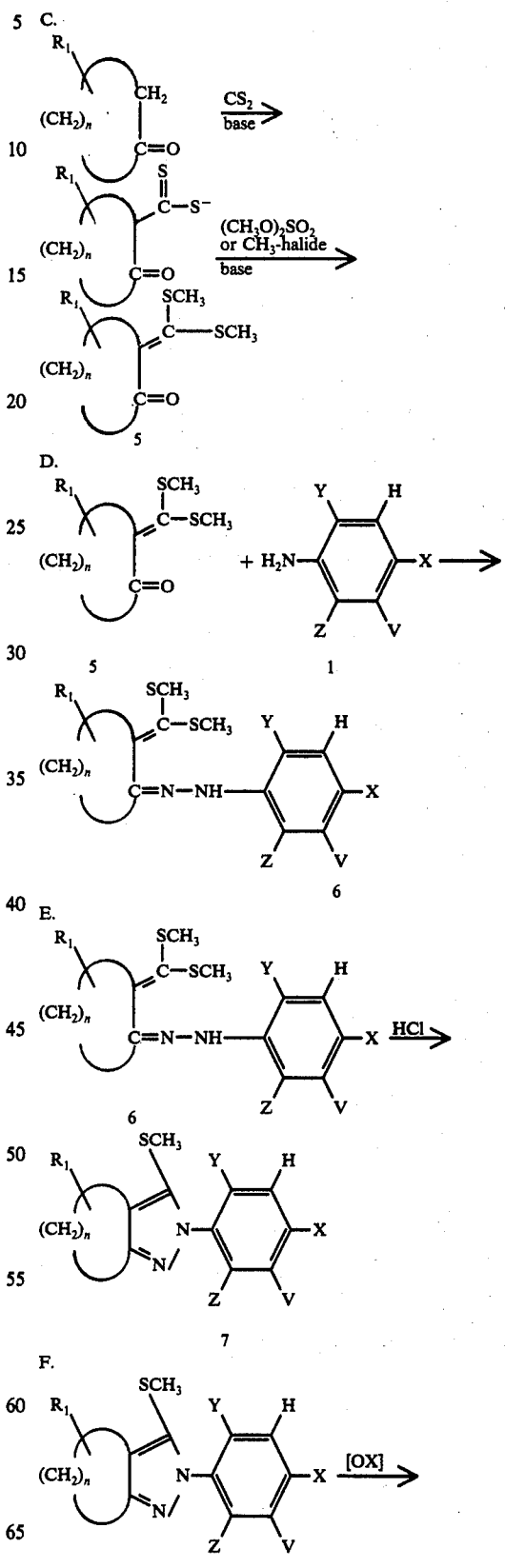

Alternatively, the hydrazone may be isolated and subsequently cyclized by treatment with two equivalents of n-butyl lithium in a solvent such as THF at temperatures of 0°–60° C. for a period of 2–18 hours.

The pyrazolones 3 where n is 3 are isolated by pouring the reaction mass into water, separating the organic layer and acidifying the aqueous layer with a mineral acid, i.e., HCl, H₂SO₄. From the acidified aqueous layer the desired product is obtained by filtration, centrifugation, extraction or other similar techniques.

The novel cycloalkanapyrazoles of Formula I, where Q is methoxy, are obtained by reacting the annelated pyrazolones 3 with dimethyl sulfate or methyl halides in the presence of base.

The procedure described by M. Saquet and M. A. Thuillier, C. R. Acad. Sci., Paris, Ser. C., 1968, 266 (4), 290 and references therein can be used to prepare the annelated pyrazoles of Formula I, where Q is methylthio, as outlined in Equations C, D and E. The cycloalkanone is condensed with carbon disulfide under alkaline conditions and alkylated. The resulting 2-[(bis-methylthio)methylene]cycloalkanone 5 is condensed with an aromatic hydrazine and the resulting 2-[(bismethylthio)methylene]cycloalkanone aryl hydrazone, 6, is cyclized with hydrochloric acid to form the annelated 3-methylthiopyrazoles, 7.

Oxidation of the methylthio function to a methylsulfinyl (Q = —S(O)—CH₃) and methylsulfonyl (Q = S(O)₂—CH₃) function is accomplished with m-chloroperbenzoic acid (Equation F) by the procedure described by A. Fischer, R. Kropp and F. Reicheneder, German Offenlegungsschrift 2,409,753.

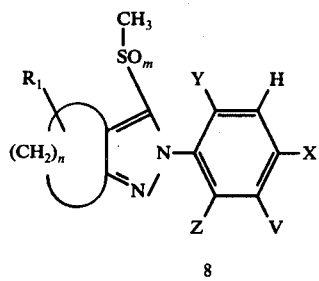

8 where m, n, R₁, V, X, Y, Z are defined as above.

The intermediate β-keto esters $\underline{2}$ are commercially available or are prepared by methods described in the literature: G. Stork et al., J. Am. Chem. Soc., 85, 207 (1963). The general procedure is shown in Equations $\underline{G}$, $\underline{H}$ and $\underline{J}$:

G.

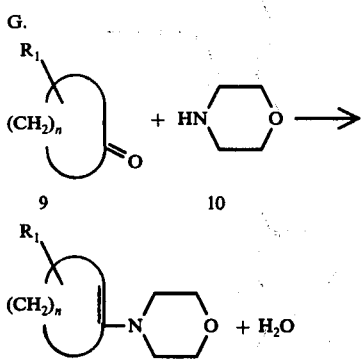

H.

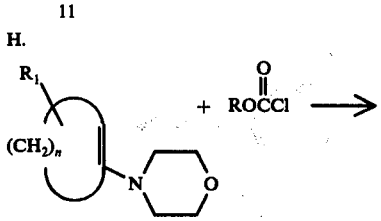

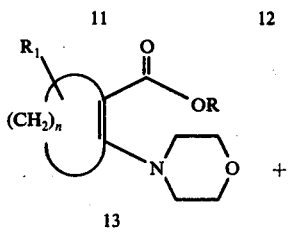

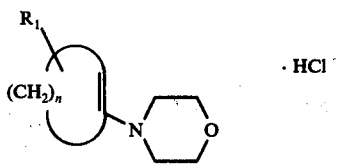

J.

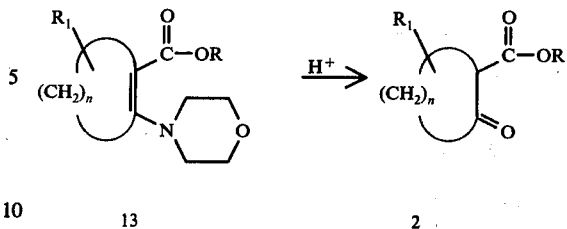

The enamine $\underline{11}$ of the cyclic ketone is prepared by heating the ketone $\underline{9}$ and morpholine $\underline{10}$ (pyrrolidine may also be used) in an appropriate solvent, such as benzene, toluene, or chlorobenzene, with simultaneous removal of water from the reaction by azeotropic distillation (Equation $\underline{G}$). The alkyl chloroformate $\underline{12}$ is added to the enamine $\underline{11}$ and this mixture is heated at a temperature from 70° C. to the boiling point of the solvent for a period of 1-10 hr. (Equation $\underline{H}$). The enamine hydrochloride $\underline{14}$ which is produced as a by-product in the reaction is removed by filtration. The morpholine enamine $\underline{13}$, which is contained in the organic filtrate, is converted to the β-keto ester $\underline{2}$ by hydrolysis with aqueous mineral acid (e.g., hydrochloric acid) at temperatures ranging from ambient to 75° C. (Equation $\underline{J}$). The product is isolated by conventional techniques such as extraction into a suitable organic solvent followed by evaporation of the solvent. The product may be further purified by fractional distillation under reduced pressure, sublimation, or crystallization.

The use of 3-methylcyclohexanone leads to a mixture of methyl-substituted β-keto esters 2a and 2b. If this mixture of methyl-substituted β-keto esters is reacted with an aryl hydrazine, a mixture of 4- and 6-methyl-substituted-2-aryl-1,2,4,5,6,7-hexahydro-3H-indazole-3-ones (3a and 3b) is produced; subsequent treatment with dimethyl sulfate $\underline{4}$ will produce a mixture containing both the 4- and 6-methyl-substituted-3-methoxy-2-aryl-tetrahydroindazoles of this invention (Ia and Ib). If the mixture of isomeric methyl cyclohexanones is separated, then 2a and 2b will lead to 3a and 3b respectively when treated with an arylhydrazine.

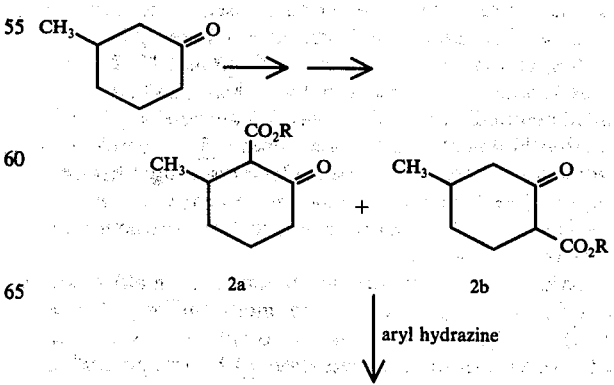

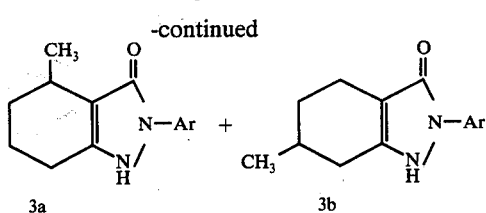

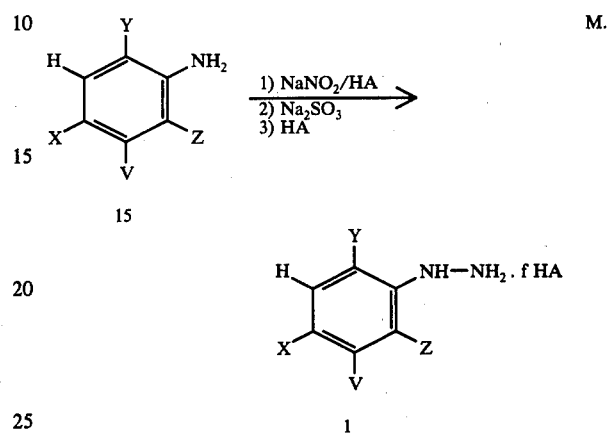

In the case of the 2- or 4-methylcyclohexanones, the β-keto ester synthesis is more specific and predominately one isomer is produced, as summarized schematically in Equations K and L. 2-Methylcyclohexanone produces 7-methyl-3-methoxy-2-aryl-4,5,6,7-tetrahydroindazole, and 4-methylcyclohexanone produces 5-methyl-3-methoxy-4,5,6,7-tetrahydroindazoles. Using the procedures outlined in Equations C, D, E and F, a 3-methylthio, 3-methylsulfinyl or 3-methylsulfonyl substituent can also be prepared from the appropriate methyl-substituted cyclohexanone.

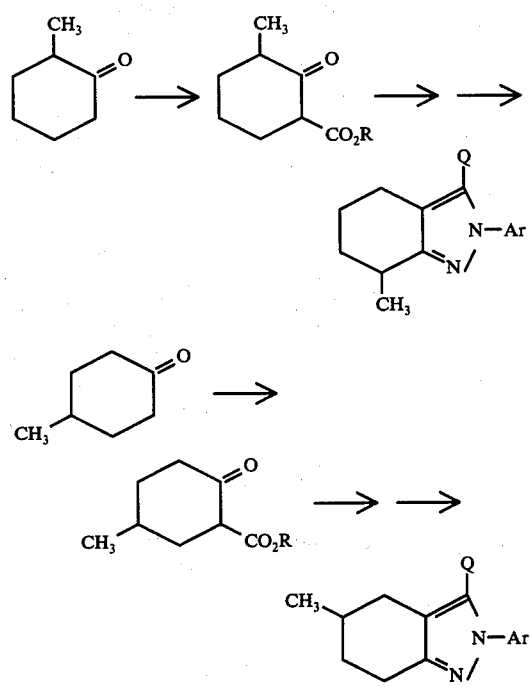

K.

L.

The required alkyl-2-oxocyclopentanecarboxylates can be prepared by methods previously described and by methods described in *Organic Reactions*, 15, 1–203 (1967).

The preparation of aryl hydrazines from anilines is well documented in the literature: G. H. Coleman, *Organic Syntheses*, Coll. Vol. I, J. Wiley & Sons, New York, p. 442 and H. Kindler et al., Fr. 1,419,092. The general procedure is illustrated in Equation M.

M.

The aniline 15 is diazotized at about −5° to 5° C. with sodium nitrite in aqueous acid (HA, where A is defined as above) such as hydrochloric acid; the resulting solution is mixed with an aqueous sodium bisulfite solution at 0°–20° C., heated to 50°–80° C. for 0.5–2 hr. and then acidified with the mineral acid to give the aryl hydrazine acid salt 1. The hydrazine salt often crystallizes directly from the reaction mixture and can be isolated by filtration or by other conventional techniques. In most instances the hydrazine salt can be used without further purification.

Certain of the hydrazines used in preparing the compounds defined by this invention are novel; e.g., 4-chloro-2-fluorophenylhydrazine hydrochloride is a novel compound which can be prepared by the method described above. The following novel hydrazines can also be prepared by this method:
4-bromo-2-fluorophenylhydrazine hydrochloride
2-fluoro-4-methoxyphenylhydrazine hydrochloride
2,4,6-trifluorophenylhydrazine hydrochloride
2-fluoro-4-nitrophenylhydrazine hydrochloride
4-cyano-2-fluorophenylhydrazine hydrochloride Also useful for preparing aryl hydrazines is the method described by M. S. Gibson et al., *J. Chem. Soc.* (C) 1970, 2106, and M. S. Gibson et al., J. Chem. Soc. (C), 1974, 215.

The aniline starting materials for these hydrazines are prepared as described below. 4-Chloro-2-fluoroaniline, for example, can be prepared from 2′-fluoroacetanilide [G. Schiemann and H. G. Baumgarten, *Chem. Berichte* 70, 1416 (1937)] by the reaction sequences shown below:

Step a

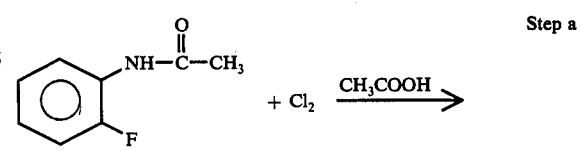

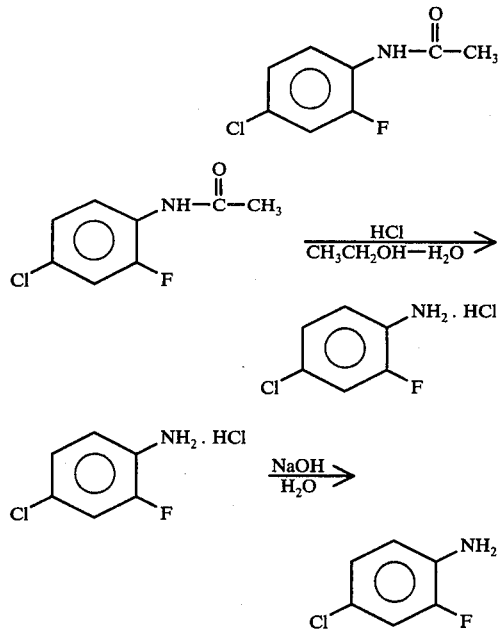

Step a

The chlorination of acetanilides in acetic acid is well known to those skilled in the art and may be carried out under the conditions taught in W. W. Reed and K. J. P. Orton, *J. Chem. Soc.*, 91, 1543 (1907) for the chlorination of acetanilide. The chlorination of 2'-fluoroacetanilide takes place at 25°–30° C. over several hours (e.g. 5) at atmospheric pressure. The resulting product is 4'-chloro-2'-fluoroacetanilide.

Step b

The chlorofluoroacetanilide is refluxed in a mixture of a lower alcohol (50%) (e.g. ethanol) and concentrated hydrochloric acid (50%) for several hours (e.g. 5 or more) at 70°–90° C. and atmospheric pressure. The solvent mixture is removed at a reduced pressure of 100 to 300 mm.Hg at a temperature of 20°–50° C. to leave a residue of the hydrochloride salt of 4-chloro-2-fluoroaniline.

Step c

After basification of an aqueous solution of the hydrochloride salt of 4-chloro-2-fluoroaniline with an alkali metal hydroxide solution, such as 50% sodium hydroxide at ambient conditions, the free 4-chloro-2-fluoroaniline is extracted into a suitable water-immiscible organic solvent such as ethyl ether or methylene chloride. The crude 4-chloro-2-fluoroaniline is isolated by removal of the organic solvent under a reduced pressure of 100 to 300 mm.Hg at 20°–50° C.

2-Fluoro-4-bromoaniline can be prepared by bromination of 2-fluoroaniline [prepared in *Chem. Berichte*, 70, 1416 (1937)] with N-bromosuccinimide as shown in the following equation.

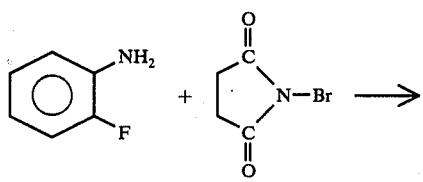
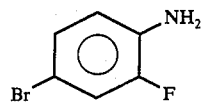

The bromination of anilines using N-bromosuccinimide in an inert organic solvent such as methylene chloride is well known to those skilled in the art, e.g., J. B. Wommack et al., *J. Het. Chem.*, 6, 243 (1969). The bromination of 2-fluoroaniline is an exothermic reaction that takes place at b 0°0 C. over several hours, e.g. 5 or more. The resulting reaction mixture is washed with water several times and dried with an appropriate drying agent such as anhydrous sodium sulfate. The 4-bromo-2-fluoroaniline is recovered by removal of the organic solvent under a reduced pressure of 100 to 300 mm. Hg at 20°–50° C.

2,4,6-Trifluoroaniline is prepared by reduction of 1,3,5-trifluoro-2-nitrobenzene [V. I. Siele and H. J. Matsugama, U.S. Department Commerce, Office Serv., *P B Rept.*, 145, 510, p. 1 (1960) or *Chem. Abst.*, 56, 15394c (1962)] using the procedures described by G. Schiemann and M. Seyhan, *Chem. Berichte*, 70, 2396 (1937).

2,4-Difluoroaniline is known to the art and can be prepared by the procedure described in G. Scheimann and M. Seyhan *Chem. Berichte*, 70, 2396 (1937).

4-Amino-3-fluorobenzonitrile, used in the preparation of 4-cyano-2-fluorophenylhydrazine hydrochloride, can be prepared from 4-bromo-2-fluoroaniline by treatment with cuprous cyanide in N-methylpyrrolidone using known procedures: L. Friedman, et al., *J. Org. Chem.*, 26, 2522 (1961). The reaction mixture is heated to reflux for several hours and then poured onto ice and sodium cyanide. The resulting solution is heated between 50°–80° C. for a period of 1–3 hours, cooled, and extracted with toluene; the toluene extract is washed with water, dried with a suitable drying agent, and evaporated to give the 4-amino-3-fluorobenzonitrile.

2-Fluoro-4-methoxyaniline, used in the preparation of 2-fluoro-4-methoxyphenylhydrazine hydrochloride, is known in the art and can be prepared by the method of H. Hodgson, et al., *J. Chem. Soc.*, 1268 (1940).

The following examples further illustrate the method for synthesis of compounds of this invention. All parts are by weight and all temperatures are in degrees centigrade.

EXAMPLE 1

Preparation of 2-(4-chloro-2-fluorophenyl)-4,5,6,7-tetrahydro-3-methoxy-2H-indazole (a) Preparation of 4-chloro-2-fluoroaniline Seventy-one parts of liquid chlorine were added to a solution of 140 parts of 2'-fluoroacetanilide in 500 parts glacial acetic acid, during one hour, at 25°–27°, with ice water cooling. While stirring for 4 hours at 25°–27°, 4'-chloro-2'-fluoroacetanilide precipitated. After collecting the product by filtration, the filtrate was poured over 2000 parts of ice. The resulting second portion of precipitated product was collected by filtration, combined with the first portion and recrystallized from 700 parts of methanol at −45° to yield 119 parts of 4'-chloro-2'-fluoroacetanilide as white crystals melting at 152°-155°.

A mixture of 119 parts of 4'-chloro-2'-fluoroacetanilide in 475 parts of ethanol and 200 parts of 37% hydrochloric acid was refluxed for 17 hours and the solvent removed under a reduced pressure of 300 mm.Hg to yield the moist, solid hydrochloride salt of 4-chloro-2-fluoro-aniline.

The moist, solid hydrochloride salt of 4-chloro-2-fluoroaniline was cooled to 10° in an ice-acetone bath and 50% aqueous sodium hydroxide was added dropwise, with stirring, until pH 11 was obtained. The resulting two-phase mixture was extracted four times; 500 parts of methylene chloride was used for each extraction. The combined organic extracts were dried over anhydrous sodium sulfate and the solvent was removed under a reduced pressure of 300 mm.Hg to leave 89 parts of light brown, oily 4-chloro-2-fluoroaniline, $n_D^{25}$ = 1.5541.

(b) Preparation of 4-chloro-2-fluorophenylhydrazine Hydrochloride 20.0 Parts of 4-chloro-2-fluoroaniline was dissolved in 80 parts of water and 34 parts of concentrated hydrochloric acid. The solution was cooled to 0°-10° and 32.2 parts of 30% sodium nitrite was added dropwise maintaining the temperature of the reaction between 0°-10°. After the addition of nitrite was completed, the solution was stirred for thirty minutes at 0°-10°. The excess nitrite was destroyed by the addition of small amounts of sulfamic acid. When a negative test with sulfone reagent was obtained, the diazonium salt was ready for reduction. For a description of the sulfone reagent see H. E. Fierz-David, et al., *Fundamental Processes of Dye Chemistry* translated from 5th Austrian Ed. by P. W. Wittam, Interscience Publishers, Inc., New York, 1949, p. 243.

In a separate vessel 35.4 parts of sodium bisulfite and 32.2 parts of 30% sodium hydroxide solution were dissolved in 140 parts of water. The solution was heated to 40°. The diazonium salt was added to the bisulfite solution over a period of 1 hour. The mixture was heated to 70° and 0.3 parts of sodium hydrosulfite was added. The pH was adjusted to 1.2 with 30 parts of concentrated hydrochloric acid; then an additional 90 parts of concentrated hydrochloric acid was added. The reaction mixture was heated for 1.5 hours at 70°, cooled slowly, and stirred overnight at room temperature.

Purification was achieved by heating the reaction mixture to 70° and filtering. The filtrate was cooled to 10° at which time the 4-chloro-2-fluorophenylhydrazine hydrochloride precipitated. This product was filtered and dried to yield 10.7 parts of yellow crystalline solid, m.p. 223°.

(c) Preparation of 2-(4-chloro-2-fluorophenyl)-1,2,4,5,6,7-hexahydro-3H-indazol-3-one 15.8 Parts of 2-fluoro-4-chlorophenylhydrazine hydrochloride, 13 parts of 2-carbethoxycyclohexanone (purchased from Aldrich Chemical Company), and 8.1 parts of triethylamine were dissolved in 100 parts of ethanol. The reactants were heated at reflux for twenty-four hours. The crude reaction mass was poured into 1000 parts of water. The resulting gummy product solidified and was filtered and dried to yield 16.1 parts of crude product with m.p. 163-170. This material was used without further purification in the next step.

By substituting 4-chlorophenylhydrazine hydrochloride in the above procedure for 4-chloro-2-fluorophenylhydrazine hydrochloride, 2-(4-chlorophenyl)-1,2,4,5,6,7-hexahydro-3H-indazol-3-one was prepared, m.p. 183.5°-185° (Lit 186°-187°, *Chem. Abs.*, 67, 11452h).

(d) Preparation of 2-(4-chloro-2-fluorophenyl)-4,5,6,7-tetrahydro-3-methoxy-2H-indazole A mixture of 2.1 parts of 2-(4-chloro-2-fluorophenyl)-1,2,4,5,6,7-hexahydro-3H-indazol-3-one, 25 parts of tetrahydrofuran and 5 parts of 10% aqueous sodium hydroxide was reacted with 1.29 parts of dimethyl sulfate. The reaction was stirred at ambient temperature for 20 hours and evaporated at 25° and 100 mm. Hg to yield 2.8 parts of a glass. This glass was chromatographed on 75 parts of Mallinckrodt Silicar CC-7 Special silica gel. The benzene eluent gave a solid which was recrystallized from etherhexane at −70° to yield 0.2 part of 2-(4-chloro-2-fluorophenyl)-4,5,6,7-tetrahydro-3-methoxy-2H-indazole melting at 100°-102°. The infrared spectrum contained no absorptions for a carbonyl, NH, or OH and the nuclear magnetic reasonance spectrum contained singlet absorption at 4.0 δ characteristic of a methoxy moiety.

By using the procedure of Example 1 with 2-carbethoxycyclohexanone, the appropriate aryl hydrazine and dimethyl sulfate, the following compounds in Formula I can be prepared.

| V | X | Y | Z |
|---|---|---|---|
| H | Cl | H | H |
| H | Br | H | H |
| H | I | H | H |
| H | CN | H | H |
| F | Cl | Cl | H |
| Cl | F | F | H |
| H | F | F | F |
| Cl | Cl | Cl | H |
| H | OCH$_3$ | F | H |
| Cl | Cl | F | H |
| H | OCH$_3$ | H | H |
| H | Br | H | H |
| H | CN | F | H |

EXAMPLE 2

Preparation of 4-bromo-2-fluoroaniline

A solution of 100 parts of 2-fluoroaniline in 400 parts of methylene chloride was cooled to 0°, and 160 parts of solid N-bromosuccinimide was added in portions over a 2-hour period. After stirring for 20 minutes, the dark red mixture was washed four times; 200 parts of cold water were used for each washing. The red organic phase was dried over anhydrous sodium sulfate and evaporated at a reduced pressure 300 mm. Hg to 164 parts of brown, oily 4-bromo-2-fluoroaniline, $n_D^{25}$: 1.5885.

EXAMPLE 3

Preparation of 4-amino-3-fluorobenzonitrile 6.8 Parts of 4-bromo-2-fluoroaniline were dissolved in 75 parts of N-methylpyrrolidone. This solution was treated with 4.2 parts of cuprous cyanide. The reaction mixture was heated to 190° for 2 hours. The reaction mass was poured onto a mixture of 200 parts of ice and 15 parts of sodium cyanide. This mixture was then heated on a steam bath for 2 hours at 60°–70°. This aqueous solution was then extracted with four 100 ml portions of toluene. The toluene extracts were combined and washed with four 300 ml portions of water followed by 100 ml of saturated NaCl. The toluene solution of the product was dried over sodium sulfate and stripped to give 2.6 parts of the desired product, m.p. 71°–73°.

EXAMPLE 4

Preparation of 2-(4-chloro-2-fluorophenyl)-2,4,5,6-tetrahydro-3-methoxycyclopentapyrazole 7.5 Parts of 4-chloro-2-fluorophenylhydrazine and 6.6 parts of methyl 2-oxocyclopentanecarboxylate (purchased from Aldrich Chemical Company) were dissolved in 200 parts of toluene. The reactants were heated at reflux for 1–2 hours; water was removed as formed. The reaction mixture was cooled to 100°, and a solution of 5.0 parts of sodium methoxide dissolved in 25 parts of methanol was added dropwise. Methanol was removed as its azeotrope with toluene. The reaction mixture was heated to an internal temperature of 110°. After cooling, the product was poured into 200 parts of ice water. The organic layer was separated, and the aqueous layer was washed twice with diethyl ether. Cold, dilute hydrochloric acid was added, with stirring, to the aqueous layer until pH was 2 attained. The resulting oily product solidified and was filtered, dried and recrystallized from acetonitrile to yield 3.3 parts of tan crystals, m.p. 157°–160°.

Alternatively, the above pyrazolone was prepared by the following procedure. 16.0 Parts of 4-chloro-2-fluorophenylhydrazine and 14.2 parts of methyl 2-oxocyclopentanecarboxylate were dissolved in 100 parts of benzene. The reaction mixture was refluxed for 1–2 hours removing water that was formed. The reaction mixture was cooled, and the solvent was removed under reduced pressure on a rotary evaporator. The resulting brown oil was dissolved in 150 parts of anhydrous tetrahydrofuran and the solution was cooled to 0° under a nitrogen atmosphere. To the cold reaction solution, 2 equivalents of n-butyllithium in hexane (purchased from Foote Mineral Company) were added at such a rate that the internal temperature was maintained at 0°–5°. The reaction mixture was allowed to warm to ambient temperature, then heated at reflux for 18 hours. The reaction mixture was cooled and poured into 200 parts ice water. The organic layer was separated, and the aqueous layer was washed twice with diethyl ether. Cold, dilute hydrochloric acid was added to the aqueous layer until pH 2 was attained. The resulting oily product solidified, and was filtered, dried, and recrystallized from acetonitrile to yield 17.5 parts of tan crystalline material, m.p. 165°–167°.

By substituting 4-chlorophenylhydrazine in the former procedure for 4-chloro-2-fluorophenylhydrazine, 2-(4-chlorophenyl)-1,4,5,6-tetrahydrocyclopentapyrazol-3(2H)-one was prepared, m.p. 193.5°–195°.

By reacting 2-(4-chloro-2-fluorophenyl)-1,4,5,6-tetrahydrocyclopentapyrazol-3(2H)-one with dimethyl sulfate in the presence of sodium hydroxide according to the procedure of Example 1(d), 2-(4-chloro-2-fluorophenyl)-2,4,5,6-tetrahydro-3-methoxycyclopentapyrazole can be made.

By using the procedure of Example 4 with 2-carbethoxycyclopentanone, the appropriate aryl hydrazine, dimethyl sulfate or a methyl halide, the following compounds of Formula I can be prepared:

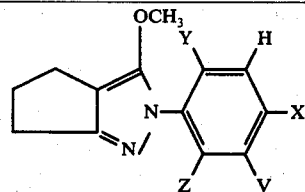

| V | X | Y | Z |
|---|---|---|---|
| H | Cl | H | H |
| H | Br | H | H |
| H | I | F | H |
| H | CN | H | H |
| F | Cl | Cl | H |
| Cl | F | F | H |
| H | F | F | F |
| Cl | Cl | Cl | H |
| H | OCH₃ | F | H |
| H | Br | F | H |
| H | OCH₃ | H | H |
| H | CN | F | H |

EXAMPLE 5

Preparation of 2-(4-chloro-2-fluorophenyl)-2,4,5,6,7,8-hexahydro-3-methoxycycloheptapyrazole By substituting 2-carbethoxycycloheptanone [prepared by the method of G. Stork, et al., J. Am. Chem. Soc., 85, 207 (1963)], for 2-carbethoxycyclohexanone in the procedure of Example 1(c) 2-(4-chloro-2-fluorophenyl)-1,4,5,6,7,8-hexahydro-3-(2H)-cycloheptapyrazole (m.p. 197°–201°) was prepared. By reacting this pyrazolone with dimethyl sulfate in the presence of sodium hydroxide as described in Example 1(d), 2-(4-chloro-2-fluorophenyl)-2,4,5,6,7,8-hexahydro-3-methoxycycloheptapyrazole can be prepared.

By using the procedure of Example 5 with 2-carbethoxycycloheptanone, the appropriate aryl hydrazine and dimethyl sulfate or a methyl halide, the following compounds of Formula I can be prepared:

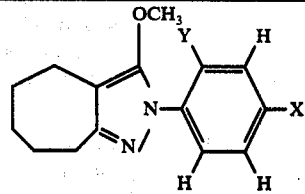

| X | Y |
|---|---|
| F | H |
| Cl | H |
| Br | H |
| Br | F |
| F | F |

EXAMPLE 6

Preparation of
2-(4-chloro-2-fluorophenyl)-2,4,5,6-tetrahydro-3-methylthiocyclopentapyrazole By substituting 4-chloro-2-fluorophenylhydrazine for phenylhydrazine in the preparation described by M. Saquet and M. A. Thuillier, *C. R. Acad. Sci.*, Paris, Ser. C., 1968, 266(4), 290, 2-(4-chloro-2-fluorophenyl)-2,4,5,6-tetrahydro-3-methylthiocyclopentapyrazole can be made.

By using the procedure of Example 6 with cyclohexanone or methylcyclohexanone and cycloheptanone or methylcycloheptanone in place of cyclopentanone, and the appropriate aryl hydrazine and dimethyl sulfate or a methyl halide, the following compounds of Formula I can be prepared:

| $R_1$ | V | X | Y | Z | n |
|---|---|---|---|---|---|
| H | H | Cl | H | H | 3 |
| H | H | Br | H | H | 4 |
| H | H | Br | F | H | 5 |
| H | Cl | F | F | H | 4 |
| $CH_3$ | H | F | F | F | 4 |
| H | H | $OCH_3$ | F | H | 3 |
| H | Cl | Cl | F | H | 3 |
| $CH_3$ | H | Br | Cl | H | 4 |
| $CH_3$ | H | CN | F | H | 4 |
| H | H | CN | H | H | 3 |
| H | F | Cl | Cl | H | 4 |
| H | H | I | H | H | 4 |

EXAMPLE 7

Preparation of
2-(4-chloro-2-fluorophenyl)-2,4,5,6-tetrahydro-3-methylsulfinylcyclopentapyrazole Using the procedure described by A. Fischer, R. Kropp and F. Reichenender in German Offenlegungsschrift 2,409,753, 2-(4-chloro-2-fluorophenyl)-2,4,5,6-tetrahydro-3-methylsulfonylcyclopentapyrazole can be made using one molar equivalent of m-chloroperbenzoic acid.

By using the procedure of Example 7 with the appropriate 3-methylthio annelated pyrazole and one molar equivalent of m-chloroperbenzoic acid, the following compounds of Formula 8 can be prepared:

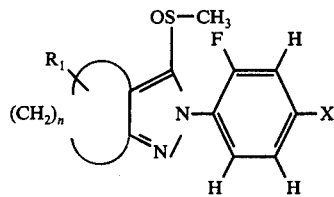

| $R_1$ | X | n |
|---|---|---|
| H | F | 3 |
| H | Cl | 4 |
| H | F | 4 |
| $CH_3$ | $OCH_3$ | 4 |
| H | $OCH_3$ | 3 |
| H | Br | 3 |
| $CH_3$ | I | 4 |
| H | CN | 4 |
| H | I | 3 |
| H | CN | 3 |

EXAMPLE 8

Preparation of
2-(4-chloro-2-fluorophenyl)-2,4,5,6-tetrahydro-3-methylsulfonylcyclopentapyrazole By the procedure using two molar equivalents of m-chloroperbenzoic acid described by A. Fischer, R. Kropp and F. Reicheneder, German Offenlegungsschrift 2,409,753, 2-(4-chloro-2-fluorophenyl)-2,4,5,6-tetrahydro-3-methylsulfonylcyclopentapyrazole can be made.

By using the procedure of Example 8 with the appropriate 3-methylthio annelated pyrazole and two molar equivalents of m-chloroperbenzoic acid the following compounds of Formula 8 can be prepared.

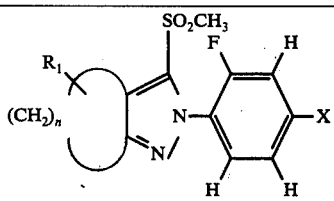

| $R_1$ | X | n |
|---|---|---|
| H | Br | 4 |
| H | F | 4 |
| $CH_3$ | Cl | 4 |
| H | $OCH_3$ | 3 |
| H | F | 3 |
| $CH_3$ | $OCH_3$ | 4 |
| H | CN | 4 |
| H | CN | 3 |
| H | Br | 3 |
| H | Cl | 4 |
| H | I | 4 |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulation broadly, contain about 0.10% to 99% by weight of active ingredient(s) and at least one of a) about 0.1% to 20% surfactant(s) and b) about 1% to 99.90% solid or liquid diluent(s). More specifically, they will usually contain these ingredients in the following approximate proportions:

|  | Percent by Weight | | |
| --- | --- | --- | --- |
|  | Active Ingredient | Diluent(s) | Surfactant(s) |
| Wettable Powders | 5-90 | 1-94 | 1-10 |
| Oil Suspensions, Emulsions, Solutions (including Emulsifiable Concentrates) | 5-50 | 40-95 | 0-15 |
| Aqueous Suspensions | 5-50 | 40-94 | 1-20 |
| Dusts | 0.10-25 | 70-99.90 | 0-5 |
| Granules and Pellets | 0.10-95 | 1-99.90 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd. ed., Dorland Books, Caldwell, N.J. Suitable diluents include finely divided or granular solids classified as attapulgites, botanicals, calcites, diatomites, dolomites, gypsum, kaolinites, limestones, mica, montmorillonoids, phosphates, pyrophyllites, sulfur, sand, talcs, tripolites, vermiculite and synthetics. These synthetics can include precipitated, hydrated silicon dioxide; precipitated, hydrated calcium silicate; precipitated calcium carbonate and synthetic organics. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation of 0° C. "McCutcheon's Detergents and Emulsifiers 1975 Annual". MC Publ. Corp., Ridgewood, New Jersey, as well as Sisely and Wood, "Encyclopedia of Surface Active Agents", Chemical Publ. Co., New York, 1964, list surfactants and recommended uses. All formulations can contain minor amounts of additives to reduce foam, caking, corrosion, microbiological growth, etc., or to mark visually the area that has been treated.

It is sometimes desirable to add ingredients to reduce the volatility of some of the compounds of this invention. Those additives can include film forming materials such as polyvinylpyrrolidones of molecular weights from about 20,000 to about 100,000; polyvinyl-alcohols of molecular weights from about 20,000 to about 150,000; and polyoxyethylenes of molecular weights from about 100,000 to about $6 \times 10^6$. These are a few examples of film forming additives. Any material which forms a film over solid active ingredient in the formulation preparation or a film over the active when sprayed and dried from a liquid formulation can be used. Other methods to reduce volatility may include the incorporation of the compounds of this invention into resins, waxes, gums, rubbers, or the like, and then preparing formulations, as has been described above, for these combinations.

Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules may be made in several ways. For example, the active ingredient may be sprayed onto a preformed granular carrier. Suitable granular carriers include those suitable diluents listed earlier having a particle size range from U.S.S. Sieve No. 200 (74 microns) to U.S.S. Sieve No. 10 (2000 microns). The preferred particle size range is from U.S.S. Sieve No. 140 (105 microns) to U.S.S. Sieve No. 20 (840 microns). Depending on the nature of the carrier, the active ingredient may remain on the surface of the carrier or be absorbed into the carrier. Usually, when the active ingredient remains on the surface of the carrier, a binding agent is used to hold the active ingredient on the surface. The binding agent should bind the active ingredient to the surface well enough so that no more than 10% of the active ingredient is removed during normal shipping and handling operations. Suitable binding agents include materials which are at least partially soluble in any liquid used in the manufacture of the granular formulation and which adhere to the granular surface. Water-soluble binders are preferred. Suitable binders include, but are not limited to, water-soluble polymers such as polyvinyl alcohols of molecular weights from about 20,000 to about 150,000; polyvinylpyrrolidones of molecular weights from about 20,000 to about 100,000 and polyoxyethylenes of molecular weights from about 100,000 to about $6 \times 10^6$. Other suitable binders include ligninsulfonates, starches, sugars and certain surface active agents listed in "McCutcheon's Detergent and Emulsifiers 1975 Annual", MC Publ. Corp., Ridgewood, New Jersey.

The active ingredient may be sprayed as a solution in a suitable solvent, which may or may not be removed from the formulation. If the active ingredient is a liquid, it may be sprayed onto or mixed with the carrier directly. If it is a solid, it may be melted and applied directly as a liquid. If very low strength granules are desired, the active ingredient may be vaporized onto the carrier. Granules may also be prepared by agglomeration techniques. For example, the active ingredient and a finely divided solid diluent may be mixed and agglomerated by techniques known in the art such as spraying with a liquid in a fluidized bed or pan granulator. The active ingredient and diluent may also be mixed with other formulation ingredients and pelletized. The pellets may then be crushed to a desired granular size. Pellets may be made by spraying the active material upon preformed granular carriers or by agglomeration techniques.

See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 9

| Granule | % |
|---|---|
| 2-(4-chloro-2-fluorophenyl)-4,5,6,7-tetrahydro-3-methoxy-2H-indazole | 10 |
| attapulgite granules (low volatile matter, 0.71–0.30 mm; U.S.S. #25–50 sieves) | 90 |

The active ingredient is warmed to approximately 105° and sprayed upon dedusted and pre-warmed attapulgite granules in a double cone blender. The granules are then allowed to cool and are packaged.

EXAMPLE 10

| Solution | % |
|---|---|
| 2-(4-chlorophenyl)-4,5,6,7-tetrahydro-3-methoxy-2H-indazole | 20 |
| dimethylformamide | 80 |

The ingredients are combined and stirred to produce a solution, which can be used for low-volume applications.

EXAMPLE 11

| Extruded Pellet | % |
|---|---|
| 2-(4-chloro-2-fluorophenyl)-4,5,6,7-tetrahydro-3-methoxy-2H-indazole | 1 |
| anhydrous sodium sulfate | 10 |
| crude calcium ligninsulfonate | 5 |
| sodium alkylnaphthalenesulfonate | 1 |
| polyoxyethylene | 1 |
| calcium/magnesium bentonite | 82 |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm. openings). The granules held on a U.S.S. No. 40 sieve (0.42 mm. openings) may be packaged for use and the fines recycled. All compounds of this invention may be formulated in this manner.

EXAMPLE 12

| Emulsifiable Concentrate | % |
|---|---|
| 2-(4-chloro-2-fluorophenyl)-4,5,6,7-tetrahydro-3-methoxy-2H-indazole | 20 |
| blend of oil soluble sulfonates and polyoxyethylene ethers | 4 |
| xylene | 76 |

The ingredients are combined and stirred until solution is complete. A fine screen filter is included in packaging operation to insure the absence of any extraneous undissolved material in the product.

EXAMPLE 13

| Aqueous Suspension | % |
|---|---|
| 2-(4-chlorophenyl)-4,5,6,7-tetrahydro-3-methoxy-2H-indazole | 40.0 |

| -continued | |
|---|---|
| Aqueous Suspension | % |
| polyacrylic acid thickener | 0.3 |
| dodecylphenol polyethylene glycol ether | 0.5 |
| disodium phosphate | 1.0 |
| monosodium phosphate | 0.5 |
| polyvinyl alcohol | 1.0 |
| pentachlorophenol | 0.4 |
| water | 56.3 |

The ingredients are ground together in a sand mill to produce particles essentially all under five microns in size.

EXAMPLE 14

| Wettable Powder | % |
|---|---|
| 2-(4-chloro-2-fluorophenyl)-4,5,6,7-tetrahydro-3-methoxy-2H-indazole | 50 |
| sodium alkylnaphthalenesulfonate | 2 |
| sodium ligninsulfonate | 2 |
| synthetic amorphous silica | 3 |
| kaolinite | 43 |

The ingredients are thoroughly blended, passed through an air mill to produce an average particle size under 15 microns, reblended, and sifted through a U.S.S. No. 50 sieve (0.3 mm opening) before packaging.

EXAMPLE 15

| High-Strength Concentrate | % |
|---|---|
| 2-(4-chlorophenyl)-4,5,6,7-tetrahydro-3-methoxy-2H-indazole | 99 |
| trimethylnonyl polyethylene glycol ether | 1 |

The surfactant is sprayed upon the active ingredient in a blender and the mixture sifted through a U.S.S. No. 40 sieve (0.42 mm. openings) prior to packaging. The concentrate may be formulated further for practical use.

EXAMPLE 16

| Low-Strength Granule | % |
|---|---|
| 2-(4-chloro-2-fluorophenyl)-4,5,6,7-tetrahydro-3-methoxy-2H-indazole | 0.5 |
| polyvinylpyrrolidone | 1 |
| attapulgite granules (low volatile matter, 0.59–0.25 mm; USS #30–60 mesh size) | 98.5 |

Forty grams of a solution containing 2.5% 2-(4-chloro-2-fluorophenyl)-4,5,6,7-tetrahydro-3-methoxy-2H-indazole and 5% polyvinylpyrrolidone dissolved in methyl alcohol are slowly atomized onto a fluidized bed of attapulgite granules (197 g). Fluidization of the granules is continued after atomization is complete and until all the methyl alcohol is evaporated from the granules. The granules are packaged for use.

EXAMPLE 17

| Extruded Pellet | % |
|---|---|
| 2-(4-chlorophenyl)-4,5,6,7-tetrahydro-3-methoxy-2H-indazole | 25 |
| anhydrous sodium sulfate | 10 |
| crude calcium ligninsulfonate | 5 |
| sodium alkylnaphthalenesulfonate | 1 |
| calcium/magnesium bentonite | 59 |

The ingredients are blended, hammer milled and moistened with about 10-12% water. The mixture is then extruded as cylinders about 3 mm. in diameter which are cut to be about 3 mm. long. These pellets may be used directly after drying or the dried pellets may be crushed to pass a U.S.S. No. 20 sieve (0.84 mm. opening). The pellets retained on a U.S.S. No. 40 sieve (0.42 mm. openings) may be packaged for use and the fines recycled.

EXAMPLE 18

| Granule | % |
|---|---|
| 2-(4-chloro-2-fluorophenyl)-4,5,6,7-tetrahydro-3-methoxy-2H-indazole | 2 |
| attapulgite granules (low volatile matter, 0.71-0.30 mm.; USS #25-50 mesh sieves) | 98 |

The active ingredient is warmed to approximately 105° and sprayed upon the dedusted and prewarmed granules in a double cone blender. The granules are allowed to cool and are packaged for use.

EXAMPLE 19

| Low Strength Granules | % |
|---|---|
| 2-(4-chloro-2-fluorophenyl)-4,5,6,7-tetrahydro-3-methoxy-2H-indazole | 0.2 |
| anhydrous sodium sulfate | 10 |
| crude calcium ligninsulfonate | 5 |
| sodium alkylnaphthalenesulfonate | 1 |
| finely divided attapulgite clay | 83.8 |

The ingredients are blended, hammer milled and placed in a fluidized bed granulator. Water is aspirated into the fluidized bed of powder until small granules are formed. Water aspiration is then stopped, but fluidization is continued to dry the formed granules. The granules are removed from the granulator and screened to pass a U.S.S. Sieve No. 20 (0.84 mm. openings). Granules retained on a U.S.S. Sieve No. 40 (0.42 mm. openings) are packaged for use. Granules larger than 0.84 mm. are ground and recycled. Fines smaller than 0.42 mm. are also recycled.

EXAMPLE 20

| Extruded Pellet | % |
|---|---|
| 2-(4-chlorophenyl)-4,5,6,7-tetrahydro-3-methoxy-2H-indazole | 0.1 |
| anhydrous sodium sulfate | 10 |
| crude calcium ligninsulfonate | 5 |
| sodium alkylnaphthalenesulfonate | 1 |
| polyoxyethylene | 1 |
| calcium/magnesium bentonite | 82.9 |

The ingredients are blended, hammer milled and then moistened with about 12% water. The moist mixture is extruded as cylinders about 1 mm. diameter and 2 mm. long. These small pellets are dried and packaged. They are applied directly.

EXAMPLE 21

| Low Strength Granules | % |
|---|---|
| 2-(4-chloro-2-fluorophenyl)-4,5,6,7-tetrahydro-3-methoxy-2H-indazole | 0.1 |
| dimethylformamide | 5 |
| attapulgite granules (low volatile matter, 0.59-0.25 mm; USS Sieve No. 30-60) | 94.9 |

The active ingredient is dissolved in dimethylformamide. This solution is very slowly atomized onto a rapidly tumbling bed of the attapulgite granules. After application of the active ingredient is complete, the formulation is blended for a few additional minutes. The dimethylformamide is not removed from the formulation. The granules are packaged for use.

EXAMPLE 22

| Emulsifiable Concentrate | % |
|---|---|
| 2-(4-chlorophenyl)-4,5,6,7-tetrahydro-3-methoxy-2H-indazole | 20 |
| blend of oil-soluble sulfonate with polyoxyethylene ethers | 6 |
| aromatic hydrocarbon solvent with a tag closed cup flash point between 100 and 115° F. | 74 |

The ingredients are combined and stirred until solution is complete. The solution is filtered prior to packaging through a fine screen filter to remove any extraneous undissolved material.

EXAMPLE 23

| Low Strength Granules | % |
|---|---|
| 2-(4-chlorophenyl)-4,5,6,7-tetrahydro-3-methoxy-2H-indazole | 0.1 |
| sodium ligninsulfonate | 5 |
| preformed sand granules having a particle size distribution from USS Sieve No. 140 (105 microns) to USS Sieve No. 50 (297 microns) | 94.9 |

The active ingredient and sodium ligninsulfonate are dissolved in methyl alcohol. This solution is slowly sprayed onto a tumbling bed of the sand granules. After spraying is complete, the tumbling granules are warmed to remove the methyl alcohol. The resulting granules are packaged for use.

Compositions can contain, in addition to the active ingredients of this invention, other conventional agricultural chemicals such as fertilizers, plant growth modifiers or herbicides.

For example, the compounds of Formula I can be combined with the following herbicides:

(1) 5-tert-butyl-3-(2,4-dichloro-5-isopropoxyphenyl)-1,3,4-oxadiazol-2-one;
(2) 6-methylthio-2,4-bis(ethylamino)-s-triazine;
(3) 3-isopropyl-(1H)-benzo-2,1,3-thiodiazin-4-one-2,2-dioxide;
(4) 2,4-dichlorophenoxyacetic acid and related esters and salts.

Combinations with wheat herbicides:

(1) 2,4-dichlorophenoxyacetic acid and related esters and salts;
(2) S-(2,2,3-trichloroallyl)-diisopropylthiocarbamate;
(3) Methyl 2-[4-(2,4-dichlorophenoxy(phenoxy)]-propanoate;
(4) 1,2-dimethyl-3,5-diphenyl-1H-pyrazolium methyl sulfate;
(5) 4-chloro-2-butynyl 3-chlorocarbanilate.

The compounds of Formula I can also be combined with other herbicides and are particularly useful in combination with bromacil [3-(sec-butyl)-5-bromo-6-methyluracil], diuron [3-(3,4-dichlorophenyl)-1,1-dimethylurea], 3-cyclohexyl-1-methyl-6-dimethylamino-s-triazine-2,4(1H,3H)-dione paraquat [1,1'-dimethyl-4,4'-bipyridinum ion], m-(3,3-dimethylureido) phenyl tert-butylcarbamate, 2-methyl-4-chlorophenoxyacetic acid, its salts or esters, 4-amino-6-tert-butyl-3-methylthio-as-triazin-5(4H)-one, aryl 4-nitrophenyl ethers such as 2,4,6-trichlorophenyl 4-nitrophenyl ether and 2,4-dichlorophenyl 4-nitrophenyl ether for controlling a broad spectrum of weeds.

The agricultural chemicals listed above are exemplary of the compounds which can be mixed with the active compounds and are not intended to limit the invention in any way.

EXAMPLE 24

For industrial use, a granule may be made from

| | |
|---|---|
| 2-(4-chloro-2-fluorophenyl)-4,5,6,7-tetra-hydro-3-methoxy-2H-indazole | 5% |
| 3-cyclohexyl-1-methyl-6-dimethylamino-S-triazine-2,4(1H,3H)-dione | 5% |
| #25–50 attapulgite granules | 90% |

The active ingredients are mixed and then warmed to approximately 105° and sprayed onto the dedusted and prewarmed granules in a double cone blender. The treated granules are then allowed to cool and are packaged.

Utility

The compounds of Formula I are useful for the selective preemergence control of undesired vegetation in crops such as rice, wheat, and peanuts. Furthermore, compounds of this invention can be used as directed treatments for the pre/postemergence control of weeds in various crops including soybeans, peanuts, cotton, garden beans and row-planted rice.

The compounds of this invention are useful for the control of weeds in transplanted crops such as rice, tobacco, tomatoes, cabbage, sweet potatoes, lettuce, celery, peppers, and eggplant. The treatment may be applied to the soil surface prior to transplanting and the crop transplanted through the treated soil or it may be soil incorporated prior to transplanting and the crop set in the treated soil. It may be applied after the crop is transplanted if care is taken to keep the chemical off the crop.

The precise amount of the compounds of Formula I to be used in any given situation will vary according to the particular end result desired, the use involved, the crop and weed species, and soil involved, the formulation used, the mode of application, prevailing weather conditions, foliage density and the like factors. Since so many variables play a role, it is not possible to state a rate of application suitable for all situations. Broadly speaking, the compounds of the invention are used at levels of about 0.1 to about 15 kilograms, preferably about 0.25 to about 10, per hectare. The lower rates in this range will generally be selected on lighter soils, at levels of about 0.1 to about 15 kilograms per hectare, preferably about 0.25 to about 10 kilograms per hectare. The lower rates in this range will generally be selected on lighter soils, soils low in organic matter content, or in situations where maximum persistence is not necessary.

Herbicidal activity of compounds of this invention was discovered in greenhouse tests.

Procedure Test 1

Seeds of crabgrass (Digitaria spp.), barnyardgrass (*Echinochloa crusgalli*), wild oats (*Avena fatua*), Cassia *tora*, morningglory (Ipomoea sp.), cocklebur (Xanthium sp.), sorghum, corn, soybean, rice, wheat and nutsedge tubers were planted in a growth medium and treated preemergence with the chemicals dissolved in a nonphytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, then all species were compared to controls and visually rated for response to treatment.

Ratings for compounds tested by this procedure are recorded in Table I. Plant response was expressed on a scale extending from 0 = no injury to 10 = complete kill. Letter symbols used had the following meanings: B = burn, G = growth retardation, C = necrosis/chlorosis, E = emergence inhibition, D = defoliation, and H = formative effect (malformation or hormone type).

Table II is presented to further illustrate the biological activity of the compounds of this invention. The data illustrate the herbicidal efficacy of the compounds with selectivity for an important crop, rice.

The test compounds were applied in a nonphytotoxic solvent to soil pots containing seeds of an intermediate hybrid rice, japonica rice, barnyardgrass (*Echinocloa crusgalli*), morningglory (Ipomea sp.), wheat, wild oats (*Avena fatua*), downy brome (*Bromus tectorum*), and cheat (*Bromus secalinus*). In addition, curly indigo (*Aeschynomene virginica*) seeds were included in some instances, as were established plantings (post-emergence) of some or all of the species mentioned above. The plants were maintained in a greenhouse (glasshouse), and visual plant response ratings (as described in Table I) were taken about three weeks after application.

It should be noted that these compounds at a low concentration virtually eliminated the undesirable vegetation, e.g., barnyardgrass, but had relatively little effect on the crops, e.g., rice.

An additional table, Table III, is presented to further illustrate the biological activity of the compounds of the present invention. The data illustrate the herbicidal efficacy of the compounds with selectivity for rice in paddy culture.

A rice paddy was constructed using a tub containing soil and barnyardgrass (*Echinochloa crusgalli*) seeds, and japonica rice plants which were transplanted into the paddy soil when in the two to three leaf stage. The water level was maintained a few centimeters above the soil surface. Test samples were applied directly into the paddy water, and plant response ratings were taken three to six weeks later.

It should be noted that these compounds at a low application rate controlled the undesirable vegetation, e.g., barnyardgrass, and did not injure paddy rice at many times that rate.

TABLE I

Post Emergence

| Compound | kg/ha | Bush Bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| [structure: tetrahydrocinnoline with OCH₃, N-(4-chloro-2-fluorophenyl)] | 2 | 9B | 9B | 10B | 10B | 9B | 4B | 9B | 10B | 9B | 7B | 10B | 9B | 10B | 10B |
| [structure: S-CH₃ tetrahydroindazole, N-(4-chloro-2-fluorophenyl)] | 0.4 | 8B | 9B 9D | 7B | 7B | 5B | 2B | 8B | 10B | 6B | 4B | 4B | 9B | 5B | 8B |
| [structure: SO₂-CH₃ tetrahydroindazole, N-(4-chloro-2-fluorophenyl)] | 0.4 | 9B | 5B 5D | 9B | 1B | 1B | 0 | 1B | 2B | 3B | 1B | 1B | 1B | 1B | 1B |
| [structure: OCH₃ tetrahydroindazole, N-(4-chlorophenyl)] | 2 | 9B | 8B 6D | 8B | 4B | 4B | 1B | 5B | 9B | 5B | 7B | 5B 9H | 4B | 4B | 5B |

Pre-Emergence

| Compound | kg/ha | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|
| [structure: tetrahydrocinnoline with OCH₃, N-(4-chloro-2-fluorophenyl)] | 2 | 1C 5G | 9C | 9C | 2C | 10C | 10C | 10C | 9C | 9C | 10C | 9C | 10C |
| [structure: S-CH₃ tetrahydroindazole, N-(4-chloro-2-fluorophenyl)] | 0.4 | 5G | 4G | 0 | 0 | 2G | 10C | 9C | 7C | 2C 8H | 5G | 6C | 9C |
| [structure: SO₂-CH₃ tetrahydroindazole, N-(4-chloro-2-fluorophenyl)] | 0.4 | 0 | 0 | 0 | 0 | 4G | 4C | 1C | 3C | 0 | 0 | 0 | 0 |
| [structure: OCH₃ tetrahydroindazole, N-(4-chlorophenyl)] | 2 | 0 | 0 | 0 | 0 | 0 | 10E | 6C | 5C | 3C 8H | 2G | 5C | 1C |

TABLE II

| Compound | kg ai/ha | PRE-EMERGENCE ||||||||| POST EMERGENCE |||||
|---|---|---|---|---|---|---|---|---|---|---|---|---|---|---|
| | | Inter-mediate Rice | Japonica Rice | Barn-yard Grass | Curly Indigo | Morning Glory | Wheat | Wild Oats | Bromus Tectorum | Bromus Secalinus | Inter-mediate Rice | Japonica Rice | Barn-yard Grass | Curly Indigo | Morning Glory |
| OCH₃–C(=N–N=)–(4-Cl,2-F-phenyl), cyclohexene-fused | 1/8 | 0 | 0 | 7E | 0 | 0 | | | | | 0 | 0 | 0 | 0 | 0 |
| | 1/2 | 0 | 0 | 10E | 0 | 0 | | | | | 0 | 0 | 0 | 0 | 4G |
| S–CH₃–C(=N–N=)–(4-Cl,2-F-phenyl), cyclohexene-fused | 1/16 | 0 | 0 | 5C | — | 0 | 0 | 0 | 0 | 0 | | | | | |
| | 1/8 | 0 | 0 | 8C | — | 0 | 0 | 0 | 0 | 0 | | | | | |
| | 1/4 | 0 | 0 | 9C | — | 0 | 0 | 3G | 3G | 0 | | | | | |
| | 1/2 | 0 | 0 | 10C | — | 0 | 0 | 0 | 6C | 3G | | | | | |
| OCH₃–C(=N–N=)–(4-Cl-phenyl), cyclohexene-fused | 1/2 | 0 | 0 | 0 | — | 0 | | | | | 0 | 0 | 0 | — | 4G |
| | 2 | 0 | 0 | 7G | — | 0 | | | | | 0 | 0 | 7C | — | 10C |

TABLE III

| Compound | Rate, kg ai/ha | Japonica Rice | Barnyard grass |
|---|---|---|---|
| 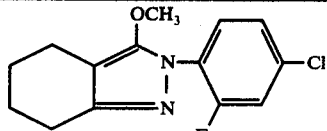 | 1/32<br>1/16<br>1/8 | 0<br>0<br>0 | 10C<br>10C |
| 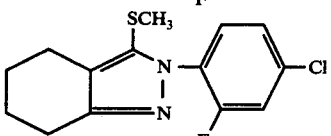 | 1/32<br>1/16<br>1/8<br>1/4 | 0<br>0<br>0<br>0 | 8G<br>8G<br>9G<br>10C |

What is claimed is:

1. A compound of the formula

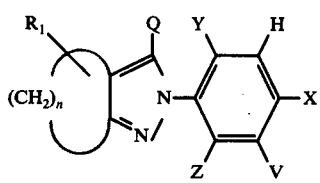

where
n is 3, 4 or 5;
Q is —O—CH₃ or —S—CH₃—;
R₁ is hydrogen or methyl;
V is hydrogen, fluorine or chlorine;
X is fluorine, chlorine, bromine, iodine, cyano or methoxy;
Y is hydrogen, fluorine or chlorine; and
Z is hydrogen or fluorine; and
with the proviso that:
(a) when n is 3, R₁ is hydrogen, and when V is fluorine or chlorine, X is fluorine, chlorine or bromine and Z is hydrogen;
(b) when n is 4 and V is fluorine or chlorine, X is fluorine, chlorine or bromine and Z is hydrogen; and
(c) when n is 5, R₁ is hydrogen, Y is hydrogen or fluorine, Z and V are hydrogen, X is fluorine, chlorine or bromine.

2. A compound of claim 1 wherein n is 3 or 4.

3. A compound of claim 1 wherein Q is methoxy or methylthio.

4. A compound of claim 1 wherein Y is hydrogen or fluorine, V is hydrogen, and Z is hydrogen.

5. A compound of claim 1 wherein R₁ is hydrogen.

6. A compound of claim 1 wherein n is 3 or 4, Q is methoxy or methylthio, and R₁ is hydrogen.

7. A compound of claim 1 wherein n is 4, Q is methoxy or methylthio, V is hydrogen, X is fluorine, chlorine or bromine, Y is hydrogen or fluorine, Z is hydrogen and R₁ is hydrogen.

8. The compound of claim 1, 2-(4-Chloro-2-fluorophenyl)-4,5,6,7-tetrahydro-3-methoxy-2H-indazole.

9. The compound of claim 1, 2-(4-Chlorophenyl)-4,5,6,7-tetrahydro-3-methoxy-2H-indazole.

10. The compound of claim 1, 2-(4-Chloro-2-fluorophenyl)-4,5,6,7-tetrahydro-3-methylthio-2H-indazole.

11. A composition for the control of undesirable vegetation consisting essentially of a herbicidally effective amount of a compound of claim 1 and at least one of (a) a surface-active agent and (b) a solid or liquid diluent.

12. A composition for the control of undesirable vegetation consisting essentially of a herbicidally effective amount of a compound of claim 2 and at least one of (a) a surface-active agent and (b) a solid or liquid diluent.

13. A composition for the control of undesirable vegetation consisting essentially of a herbicidally effective amount of a compound of claim 3 and at least one of (a) a surface-active agent and (b) a solid or liquid diluent.

14. A composition for the control of undesirable vegetation consisting essentially of a herbicidally effective amount of a compound of claim 4 and at least one of (a) a surface-active agent and (b) a solid or liquid diluent.

15. A composition for the control of undesirable vegetation consisting essentially of a herbicidally effective amount of a compound of claim 5 and at least one of (a) a surface-active agent and (b) a solid or liquid diluent.

16. A composition for the control of undesirable vegetation consisting essentially of a herbicidally effective amount of a compound of claim 6 and at least one of (a) a surface-active agent and (b) a solid or liquid diluent.

17. A composition for the control of undesirable vegetation consisting essentially of a herbicidally effective amount of a compound of claim 7 and at least one of (a) a surface-active agent and (b) a solid or liquid diluent.

18. A composition for the control of undesirable vegetation consisting essentially of a herbicidally effective amount of the compound of claim 8 and at least one of (a) a surface-active agent and (b) a solid or liquid diluent.

19. A composition for the control of undesirable vegetation consisting essentially of a herbicidally effective amount of the compound of claim 9 and at least one of (a) a surface-active agent and (b) a solid or liquid diluent.

20. A composition for the control of undesirable vegetation consisting essentially of a herbicidally effective amount of the compound of claim 10 and at least one of (a) a surface-active agent and (b) a solid or liquid diluent.

21. A method for the control of undesirable vegetation comprising applying to the locus of such undesirable vegetation a herbicidally effective amount of a compound of claim 1.

22. A method for the control of undesirable vegetation comprising applying to the locus of such undesirable vegetation a herbicidally effective amount of a compound of claim 2.

23. A method for the control of undesirable vegetation comprising applying to the locus of such undesirable vegetation a herbicidally effective amount of a compound of claim 3.

24. A method for the control of undesirable vegetation comprising applying to the locus of such undesirable vegetation a herbicidally effective amount of a compound of claim 4.

25. A method for the control of undesirable vegetation comprising applying to the locus of such undesirable vegetation a herbicidally effective amount of a compound of claim 5.

26. A method for the control of undesirable vegetation comprising applying to the locus of such undesirable vegetation a herbicidally effective amount of a compound of claim 6.

27. A method for the control of undesirable vegetation comprising applying to the locus of such undesirable vegetation a herbicidally effective amount of a compound of claim 7.

28. A method for the control of undesirable vegetation comprising applying to the locus of such undesirable vegetation a herbicidally effective amount of the compound of claim 8.

29. A method for the control of undesirable vegetation comprising applying to the locus of such undesirable vegetation a herbicidally effective amount of the compound of claim 9.

30. A method for the control of undesirable vegetation comprising applying to the locus of such undesirable vegetation a herbicidally effective amount of the compound of claim 10.

31. A method for the control of undesirable vegetation in crops comprising applying to the locus of such undesirable vegetation a herbicidally effective amount of a compound of claim 1.

32. The method of claim 31 wherein such crops are rice or wheat.

33. The method of claim 31 wherein such crop is rice.

34. The method of claim 31 wherein such crop is wheat.

35. A method for the control of undesirable vegetation in rice, which comprises applying to the locus of such undesirable vegetation a herbicidally effective amount of the compound of claim 8.

36. The method of claim 35 wherein the undesirable vegetation is barnyardgrass.

37. A method for the control of undesirable vegetation in transplanted crops comprising applying to the locus of such undesirable vegetation a herbicidally effective amount of a compound of claim 1.

38. A method for the control of undesirable vegetation in transplanted crops comprising applying to the locus of such undesirable vegetation a herbicidally effective amount of the compound of claim 8.

39. A method for the control of undesirable vegetation in paddy rice which comprises applying to the locus of such undesirable vegetation a herbicidally effective amount of a compound of claim 1.

40. A method for the control of undesirable vegetation in paddy rice which comprises applying to the locus of such undesirable vegetation a herbicidally effective amount of the compound of claim 8.

41. A method for the control of undesirable vegetation in wheat, comprising applying to the locus of such undesirable vegetation a herbicidally effective amount of the compound of claim 8.

42. A compound of the formula

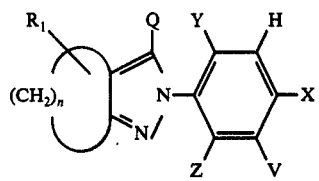

where
n is 3 or 4;
Q is $-S(O)_m-CH_3$;
m is 1 or 2;
$R_1$ is hydrogen or methyl;
V is hydrogen;
X is fluorine, chlorine, bromine, iodine, cyano or methoxy;
Y is fluorine; and
Z is hydrogen; and
with the proviso that:
(a) when n is 3, $R_1$ is hydrogen.

43. A compound of claim 42 wherein n is 3.

44. A composition for the control of undesirable vegetation consisting essentially of a herbicidally effective amount of a compound of claim 42 and at least one of (a) a surface-active agent and (b) a solid or liquid diluent.

45. A composition for the control of undesirable vegetation consisting essentially of a herbicidally effective amount of a compound of claim 43 and at least one of (a) a surface-active agent and (b) a solid or liquid diluent.

46. A method for the control of undesirable vegetation comprising applying to the locus of such undesirable vegetation a herbicidally effective amount of a compound of claim 42.

47. A method for the control of undesirable vegetation comprising applying to the locus of such undesirable vegetation a herbicidally effective amount of a compound of claim 43.

48. A method for the control of undesirable vegetation in crops comprising applying to the locus of such undesirable vegetation a herbicidally effective amount of a compound of claim 42.

49. The method of claim 48 wherein such crops are rice or wheat.

50. The method of claim 48 wherein such crop is rice.

51. The method of claim 48 wherein such crop is wheat.

52. A method for the control of undesirable vegetation in transplanted crops comprising applying to the locus of such undesirable vegetation a herbicidally effective amount of a compound of claim 42.

53. A method for the control of undesirable vegetation in paddy rice which comprises applying to the locus of such undesirable vegetation a herbicidally effective amount of a compound of claim 42.

* * * * *